US 011608484B2

(12) United States Patent
Arnold et al.

(10) Patent No.: US 11,608,484 B2
(45) Date of Patent: Mar. 21, 2023

(54) SINGLE-USE CONNECTION DEVICE

(71) Applicant: EPPENDORF AG, Hamburg (DE)

(72) Inventors: Matthias Arnold, Aachen (DE);
Sebastian Selzer, Aachen (DE); Sven Eikelmann, Petershagen (DE); Jochen Beese, Norderstedt (DE)

(73) Assignee: EPPENDORF AG, Hamburg (DE)

( * ) Notice: Subject to any disclaimer, the term of this patent is extended or adjusted under 35 U.S.C. 154(b) by 768 days.

(21) Appl. No.: 16/072,630

(22) PCT Filed: Jan. 27, 2017

(86) PCT No.: PCT/EP2017/051865
§ 371 (c)(1),
(2) Date: Jul. 25, 2018

(87) PCT Pub. No.: WO2017/129800
PCT Pub. Date: Aug. 3, 2017

(65) Prior Publication Data
US 2019/0031995 A1 Jan. 31, 2019

(30) Foreign Application Priority Data

Jan. 29, 2016 (EP) .................................... 16153294

(51) Int. Cl.
*C12M 1/00* (2006.01)
*C12M 1/12* (2006.01)
(Continued)

(52) U.S. Cl.
CPC ............ *C12M 23/28* (2013.01); *C12M 23/14* (2013.01); *C12M 23/38* (2013.01); *C12M 23/40* (2013.01);
(Continued)

(58) Field of Classification Search
CPC ...... C12M 23/28; C12M 23/14; C12M 23/38; C12M 23/40; C12M 37/02; C12M 37/04; C12M 41/44; C12M 23/42
See application file for complete search history.

(56) References Cited

U.S. PATENT DOCUMENTS

| 4,639,422 A | * | 1/1987 | Geimer ................. C12M 29/04 435/297.3 |
| 5,350,080 A | | 9/1994 | Brown et al. |

(Continued)

FOREIGN PATENT DOCUMENTS

| CN | 101693878 | 4/2010 |
| CN | 101886039 | 11/2010 |

(Continued)

OTHER PUBLICATIONS

Ting Yang et al, "Novel disposable flexible bioreactor for *Escherichia coli* culture in orbital shaking incubator," The Society for Biotechnology, Japan (2013), http://dx.doi.org.10.1016/j.jbiosc.2013.04.004.

*Primary Examiner* — William H. Beisner
*Assistant Examiner* — Danielle B Henkel
(74) *Attorney, Agent, or Firm* — Price Heneveld LLP

(57) ABSTRACT

The invention relates to a single-use connection device for insertion into a connection opening of a bioreactor, in particular in a connection opening of a top plate of a dimensionally-stable bioreactor or in a connection opening of a connection element of a pouch bioreactor. The single-use connection device is inserted in a connection opening of a top plate of a bioreactor and/or in a connection opening of a pouch reactor and is provided with multiple passages and an attachment section, wherein the single-use connection device is formed as a single piece and is made of plastic. The attachment section, on an outer peripheral surface, has an
(Continued)

attachment structure for attaching the single-use connection device in the connection opening.

15 Claims, 10 Drawing Sheets

(51) Int. Cl.
  *C12M 1/34* (2006.01)
  *C12M 3/00* (2006.01)
(52) U.S. Cl.
  CPC ............ *C12M 23/42* (2013.01); *C12M 37/02* (2013.01); *C12M 37/04* (2013.01); *C12M 41/44* (2013.01)

(56) References Cited

U.S. PATENT DOCUMENTS

| | | | |
|---|---|---|---|
| 5,368,801 | A | 11/1994 | Vaillancourt |
| 6,202,713 | B1 | 3/2001 | Drescher et al. |
| 6,604,908 | B1 | 8/2003 | Bryant et al. |
| 7,947,032 | B2 | 5/2011 | Harding et al. |
| 8,522,996 | B2 | 9/2013 | Beese et al. |
| 2003/0119201 | A1 | 6/2003 | Wolfram et al. |
| 2003/0129743 | A1 | 7/2003 | Wildi et al. |
| 2004/0029170 | A1 | 2/2004 | Wolfram et al. |
| 2005/0135975 | A1 | 6/2005 | Su et al. |
| 2008/0131957 | A1 | 6/2008 | Ryan et al. |
| 2009/0120169 | A1* | 5/2009 | Chandler, Jr. ......... G01N 11/16 29/25.35 |
| 2010/0291674 | A1* | 11/2010 | Beese .................... C12M 23/38 435/325 |
| 2010/0308051 | A1* | 12/2010 | Weber ............... B01L 3/502715 220/266 |
| 2011/0233210 | A1 | 9/2011 | Fatherazi et al. |
| 2014/0011270 | A1* | 1/2014 | Chotteau ................ C12M 27/20 435/326 |
| 2015/0132840 | A1* | 5/2015 | Arnold .................. C12M 23/42 156/60 |
| 2015/0218501 | A1* | 8/2015 | Kauling ................. C12M 21/08 435/325 |
| 2016/0108354 | A1 | 4/2016 | Kahlert et al. |
| 2019/0063420 | A1 | 12/2019 | Stobbe |

FOREIGN PATENT DOCUMENTS

| | | | |
|---|---|---|---|
| CN | 104379722 | 2/2015 | |
| CN | 104508110 | 4/2015 | |
| DE | 2137854 | 2/1973 | |
| DE | 102004059146 | 7/2005 | |
| DE | 202009015434 | 4/2010 | |
| DE | 102016015207 | 6/2018 | |
| EP | 2251407 | 11/2010 | |
| EP | 2379889 | 10/2011 | |
| EP | 2674479 | 12/2013 | |
| EP | 2853584 | 4/2015 | |
| EP | 3460036 | 3/2019 | |
| EP | 3514223 | 4/2019 | |
| JP | 2007282629 | 11/2007 | |
| JP | 2007330108 | 12/2007 | |
| JP | 2010226975 | 10/2010 | |
| JP | 2010263891 | 11/2010 | |
| JP | 4986659 | 7/2012 | |
| JP | 2013502930 | 1/2013 | |
| JP | 2014528250 | 10/2014 | |
| WO | 1999002961 | 1/1999 | |
| WO | 2006044441 | 4/2006 | |
| WO | 2008016411 | 2/2008 | |
| WO | 2010069321 | 6/2010 | |
| WO | 2011025890 | 3/2011 | |
| WO | 2011126793 | 10/2011 | |
| WO | WO-2011144561 A1 * | 11/2011 | ........... B29C 66/522 |
| WO | 2013053778 | 4/2013 | |
| WO | 2013053779 | 4/2013 | |
| WO | 2013150064 | 10/2013 | |
| WO | 2013158756 | 10/2013 | |
| WO | 2013186294 | 12/2013 | |
| WO | 2014042827 | 3/2014 | |
| WO | 2014177240 | 11/2014 | |
| WO | 2015077663 | 5/2015 | |
| WO | 2015135376 | 9/2015 | |
| WO | 2016066768 | 5/2016 | |
| WO | 2017129800 | 8/2017 | |
| WO | 2018115028 | 6/2018 | |
| WO | 2021008788 | 1/2021 | |

* cited by examiner

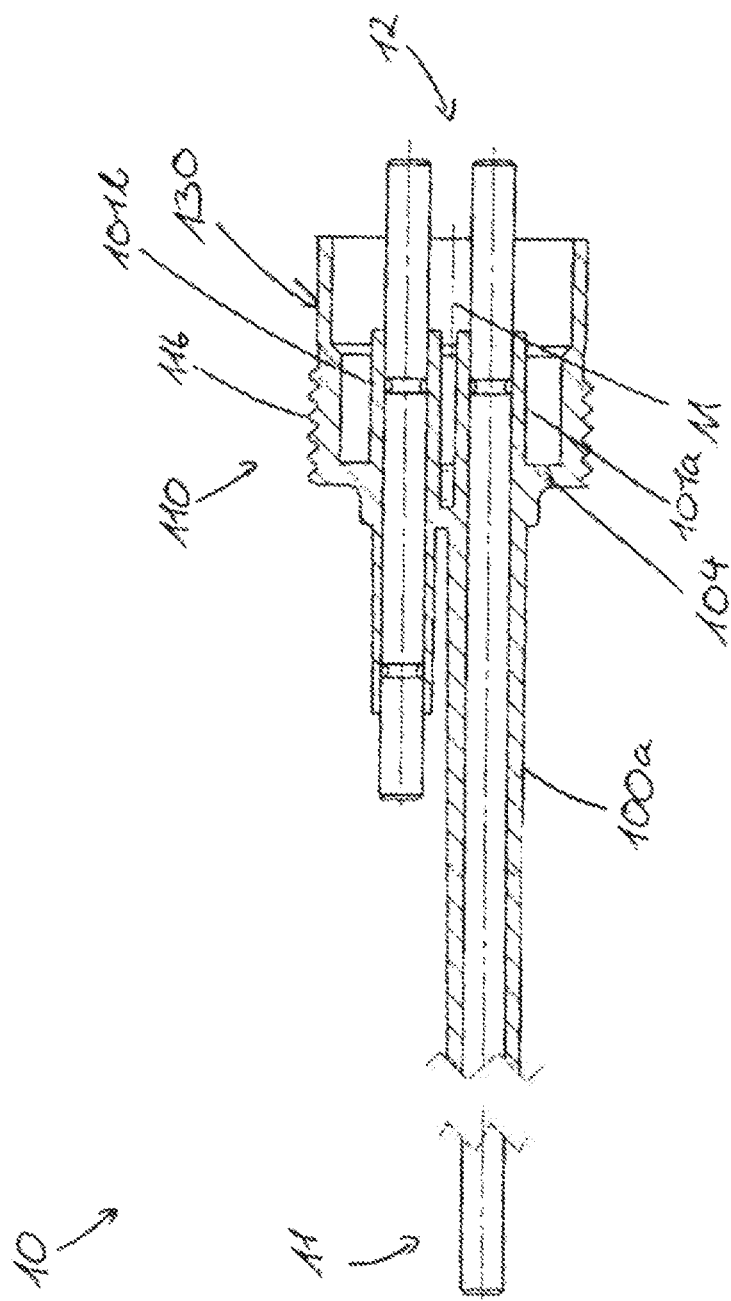

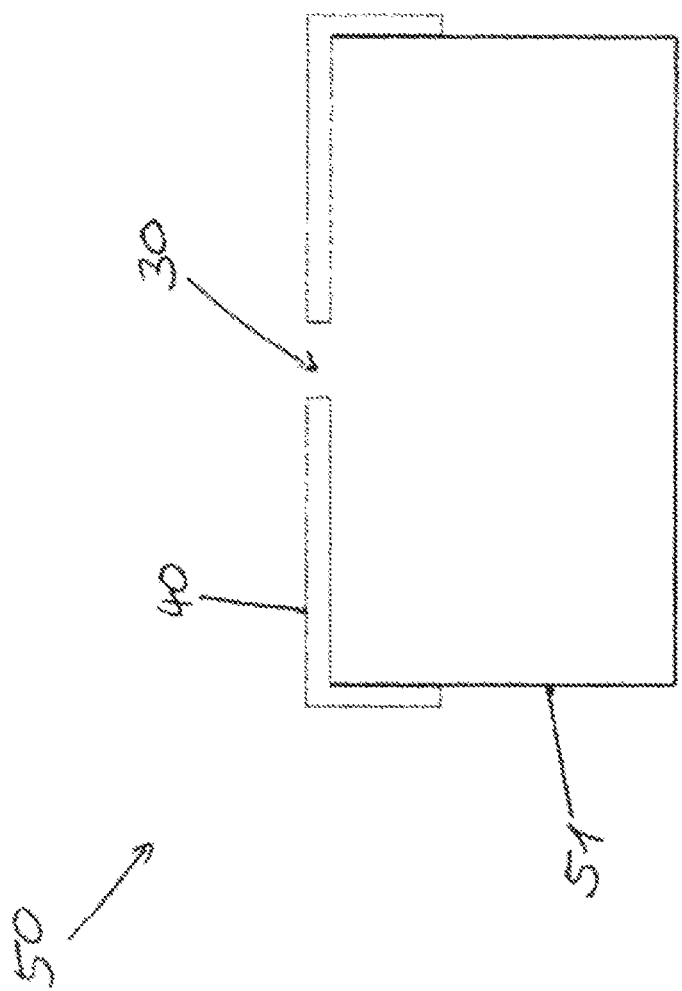

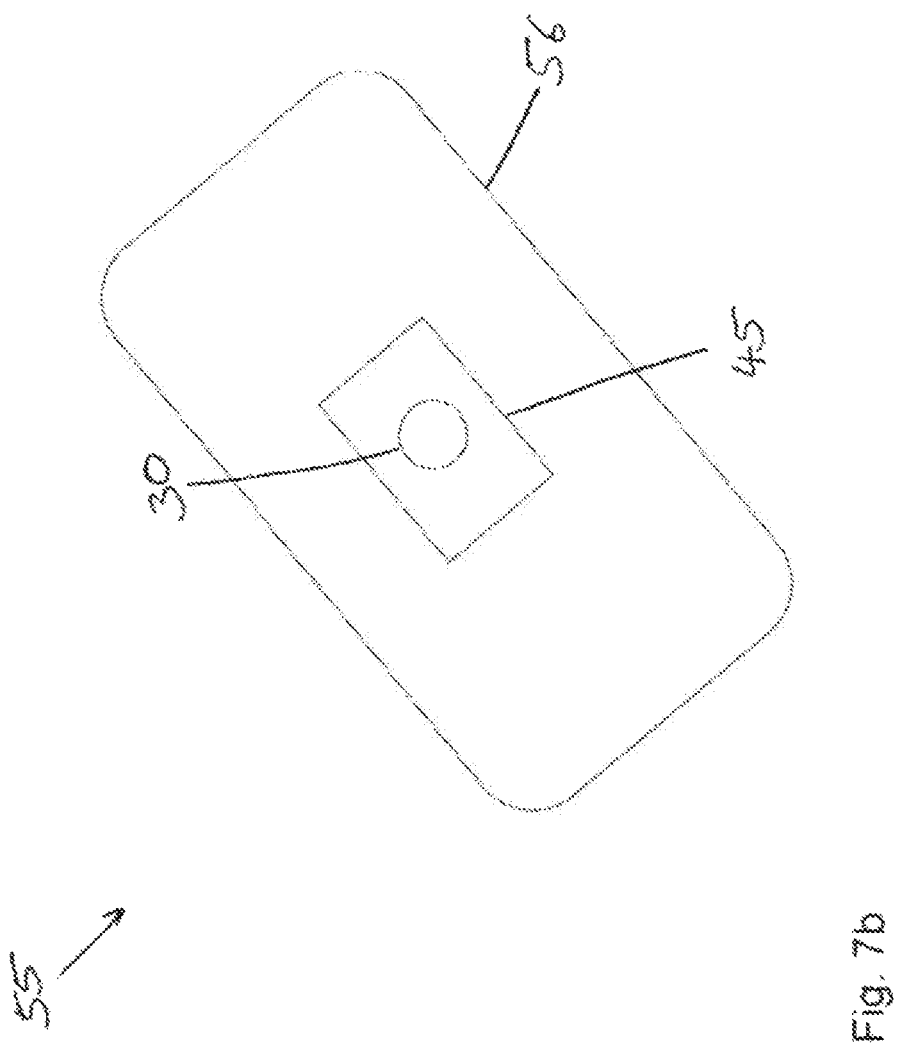

SINGLE-USE CONNECTION DEVICE

CROSS-REFERENCE TO FOREIGN PRIORITY APPLICATION

The present application claims the benefit under 35 U.S.C. § 119(b), 119(e), 120, 121, 365(c), and/or 386(c) of PCT/EP2017/051865 filed Jan. 27, 2017, which claims priority to European Patent Application No. 16153294.0 filed Jan. 29, 2016.

FIELD OF THE INVENTION

The invention relates to a single-use connection device for insertion into a connection opening of a bioreactor, in particular into a connection opening of a top plate of a dimensionally stable bioreactor and/or into a connection opening of a connection element of a pouch bioreactor. The invention also relates to a top plate for a bioreactor and to a bioreactor for cultivating microorganisms and/or cell cultures. The invention also furthermore relates to a connection element for a pouch bioreactor and to a pouch bioreactor for cultivating microorganisms and/or cell cultures.

BACKGROUND OF THE INVENTION

A microorganism is a microscopically small, normally single-cell or few-celled plant or animal organism. Microorganisms can therefore also be referred to as the entirety of all organisms that are not visible to the naked eye. These include various groups of viruses, bacteria, archaea, protozoa, fungi and microalgae. Numerous microorganisms are considered to be useful because they are advantageous for example for geochemical materials cycles, are used for the production of certain foodstuffs and are used as producers of medicines. Furthermore, pathogenic microorganisms are often grown for research purposes. The cultivation of microorganisms includes, inter alia, the creation and maintenance of conditions that ensure growth of the organisms, wherein the aim of reproducing the organisms is often also pursued.

A cell culture is the cultivation of a cell population outside an organism under controlled conditions, wherein the physiological processes of the cells are entirely or predominantly maintained. The cultivation therefore includes not only the cell population but, inter alia, also a culture medium that permits the growth, the proliferation, and the differentiation of the cell culture. Normally, culture media comprise amino acids, vitamins, inorganic salts and buffer mixtures and generally glutamine. Cell cultures are used for a wide variety of different purposes, wherein the main application is in the research and development sector. Cell cultures are likewise of high importance for the production of numerous biotechnical products.

The cultivation of microorganisms and/or cell cultures is generally performed under sterile conditions in the culture medium, which is also referred to as culture broth, in a reaction chamber in the interior of a bioreactor. At least during a certain time period of the cultivation, gaseous and/or liquid fluids are fed to the system in order to maintain the biological processes, and/or gaseous and/or liquid fluids, which may also comprise further constituents generated as a result of biological processes, are discharged.

Bioreactors, which are also referred to as fermentation reactors or fermenters, comprise in particular a vessel, in the interior of which it is sought for biological or biotechnological processes to take place, or for particular cultures, in particular microorganisms and/or cell cultures, to be cultivated, under regulated and defined conditions. The interior of the bioreactor and/or of the vessel is also referred to as a reaction chamber. The vessel generally comprises a completely or predominantly closed enclosing wall, wherein one side may also be closed off by a top plate. The vessel and/or the top plate furthermore have connection openings which serve for receiving or fastening connections. Connections serve as a connecting element between the interior space of the vessel of the bioreactor and feed lines located outside the vessel, wherein said feed lines serve for the feed of gaseous and/or liquid fluids or for the feed of solid bodies, for example sensors, into the interior space of the vessel.

Bioreactors are commonly formed from glass and/or metal, in particular rust-resistant steel. Since an individual bioreactor can be used for different biological or biotechnological processes and a sterilization must generally be performed between the different processes, the materials glass and/or metal are particularly suitable, because these materials can be well sterilized. This sterilization is preferably performed by hot steam sterilization in an autoclave. The sterilization and cleaning process may furthermore be subject to a validation, and the carrying out of said validation must be documented for each individual bioreactor.

The residues in a not fully sterilized bioreactor can distort the biological or biotechnological process performed subsequently, and thus render the results unusable. The distortion of the process by residues applies on the one hand to residues within the reactor and on the other hand also to residues in devices that are in direct and/or indirect contact with the reaction chamber of the bioreactor. These include in particular, but not exclusively, connections via which primary and secondary substances and instruments, such as for example sensors, can be introduced into the reaction chamber. Fluid lines, which may be formed as feed or discharge lines, may additionally or alternatively be attached to said connections.

Said connections are commonly located on a top plate of the bioreactor. The top plate has an areal geometry, wherein the area preferably has a substantially horizontal extent. The connections are generally attached to or in openings of the top plate. Said openings preferably have a substantially vertical passage direction.

The cumbersome sterilization, and possible additional validation thereof, can be avoided through the use of so-called single-use bioreactors. These are designed for carrying out only a single biological or biotechnological process, and are disposed of after said process has been carried out. Through the provision of a new single-use bioreactor, which has preferably been sterilized in the production process, for each process, the risk of (cross-)contamination can be reduced, and at the same time, the outlay for carrying out and documenting proper cleaning and/or sterilization of a previously used bioreactor is eliminated. Single-use bioreactors are often formed as vessels which are entirely or partially not dimensionally stable, for example as pouch bioreactors and/or as vessels with walls which, at least in sections, are not dimensionally stable.

A sterile single-use bioreactor generally comprises one or more connections via which primary and secondary substances, for example gaseous or liquid fluids, and various solid bodies, such as, for example, sensors, can be introduced into the reaction chamber.

Connections of the abovementioned type have a multiplicity of technical requirements, which furthermore have interdependencies. The imperative prerequisite of a sterile environment comprises not only the interior space of the vessel of the bioreactor, but additionally all feed lines to said interior space. This prerequisite also encompasses in particular the connections, because the connections are in direct contact with the interior space and/or conduct media or the like which pass into the interior space. It is furthermore a requirement that the connection substantially hermetically decouples the interior space of the bioreactor from the surroundings outside the bioreactor. The existing devices offer various advantages, but further improvements are desirable.

SUMMARY OF THE INVENTION

It is therefore an object of the present invention to provide a single-use connection device for insertion into a connection opening of a bioreactor, a top plate for a bioreactor, and a bioreactor for cultivating microorganisms and/or cell cultures, which alleviate or eliminate one or more of the stated disadvantages. In particular, it is an object of the invention to provide a single-use connection device for insertion into a connection opening of a bioreactor, a top plate for a bioreactor, and a bioreactor for cultivating microorganisms and/or cell cultures, which reduce the risk of contamination and nevertheless provide an inexpensive solution.

The object according to the invention is, according to a first aspect, achieved by means of a single-use connection device for insertion into a connection opening of a top plate of a bioreactor and/or into a connection opening of a pouch bioreactor, having multiple passages and a fastening section, characterized in that the single-use connection device is formed in one piece and from plastic, and the fastening section has, on an outer circumferential surface, a fastening structure for the fastening of the single-use connection device in the connection opening.

According to the invention, the single-use connection device is inserted into a connection opening of a top plate of a bioreactor and/or into a connection opening of a pouch bioreactor. The insertion means in particular that the single-use connection device is installed into a connection opening, which preferably involves the single-use connection device being embedded and/or joined and/or fitted into and/or onto the abovementioned opening. The insertion may furthermore involve the single-use connection device being detachably or non-detachably fastened to a constituent part of a bioreactor, in particular in the connection opening.

Connections may often be the cause for contaminations of the interior space of the bioreactor. The cause may be, for example, a contamination of the lines running through the connection or incomplete sealing between the outer wall of the connection and an opening, which forms a wall, in the vessel of the bioreactor. The invention is therefore based on the realization that the sterility in the bioreactor is influenced not only by the bioreactor itself, but likewise and equally by the connections and the normally complex geometry thereof. Therefore, the single-use connection device according to the invention is designed as a single-use component. A single-use component is, in the present usage situation, used only for a single use, and is subsequently disposed of. The single-use connection device is accordingly used for a single cultivation of microorganisms and/or cell cultures. This reduces the risk of contamination considerably, and no cleaning of the single-use connection device is required. Furthermore, the validation process that possibly has to be carried out is eliminated.

The abovementioned connection opening of a top plate of a bioreactor and/or of a connection element of a pouch bioreactor serves for receiving the single-use connection device. Preferably, a longitudinal axis is parallel, in an axial direction of the single-use connection device, to a passage direction of the connection opening. The cross section, orthogonal with respect to the passage direction, of the connection opening is preferably substantially circular, aside from a fastening structure which may be provided, which is preferably of complementary form with respect to the fastening structure of the single-use connection device. Said cross section of the connection opening furthermore preferably has a slot-like, triangular or polygonal cross section. The geometry and the dimensions of the cross section are preferably variable along the passage direction.

The connection opening and that section of the single-use connection device which is in contact with a wall or other delimitation of the connection opening are preferably formed such that, by means of the contact of the two components, hermetic and/or fluid-tight sealing of the connection opening can be realized, wherein use may preferably also be made of an encircling seal described further below. The bioreactor comprises a vessel and a top plate. The vessel preferably has an enclosing wall with regard to its horizontal extents. The vessel furthermore preferably has an enclosing wall with regard to a vertical extent, wherein said enclosing wall may be formed by a vessel base. The top plate as a further element of the bioreactor has the function of closing off the bioreactor. The top plate preferably has a substantially areal geometry, wherein the area preferably has a predominantly horizontal extent. The top plate furthermore has at least one connection opening.

In a further preferred design variant, the bioreactor is designed as a so-called pouch bioreactor. A pouch bioreactor is formed as a fully flexible vessel or vessel which is partially not dimensionally stable, for example as a vessel with enclosing walls which, at least in sections, are not dimensionally stable. Pouch bioreactors are generally formed as single-use bioreactors, such that cumbersome sterilization, and possibly comprehensive validation of said sterilization, can be avoided. The pouch bioreactor comprises a connection element with a connection opening.

The bioreactor comprises one or more connection openings for the attachment of single-use connection devices via which primary and secondary substances, for example gaseous or liquid fluids, and various solid bodies, such as for example sensors, can be introduced into the interior space of the bioreactor. In order that the primary and secondary substances and/or solid bodies can be introduced into the interior space of the bioreactor, the single-use connection devices have, according to the invention, multiple passages. The passages are preferably designed with an encircling wall and can receive various instruments, sensors, hoses or lines.

The passage direction of the multiple passages is preferably substantially parallel to the passage direction of the connection opening into which the single-use connection devices is inserted. It is furthermore preferable for the multiple passages to have a passage direction which is substantially parallel to a longitudinal axis of the single-use connection device. The multiple passages have in each case a first passage end and a second passage end. Between these two ends, the passage is designed with a fully encircling wall, such that a fluid that enters at the first passage end can escape only at the second passage end. The axial length of the passages may vary. Multiple passages are at least two passages, but preferably three or more passages.

The passages on the inner side, the side facing toward the bioreactor, of the top plate or of the connection element preferably correspond to devices on the outer side, the side averted from the bioreactor, of the top plate or of the connection element, such that the gaseous and/or liquid fluids and/or solid bodies can be led into and out of the reaction chamber through the passages. The passage ends on the side averted from the bioreactor are accordingly preferably designed for the connection of lines for the supply and/or discharge of the culture medium, for the provision of instruments, for example sensor arrangements, and/or for further operating and/or auxiliary means and/or substances used for carrying out the cultivation of microorganisms and/or cell cultures.

The passages, at least one of the passages, preferably project into the reaction chamber of the bioreactor to such an extent that, during an intended use of the bioreactor, said passages dip into a content, for example a liquid, arranged in the reaction chamber. The passages are in this case also referred to as immersion pipes. This has the advantage that no pipes or hoses need to be connected to that side of the single-use connection device which faces toward the interior space of the bioreactor, but the passages already formed on the single-use connection device, or the enclosing walls thereof, can rather be used. A Luer lock system is preferably provided for the fastening of further connections to the passages, in particular on a side of the single-use connection device averted from the bioreactor.

The cross sections, orthogonal with respect to the passage direction, of the multiple passages are preferably circular. It is furthermore preferably possible for the cross sections of the multiple passages to have different geometries. The diameters of the multiple passages may each be equal or different. A diameter of a single circular passage preferably amounts to 1 mm to 4 mm, furthermore preferably 1.5 to 2.5 mm, and furthermore preferably 2 mm.

The invention is based on the realization that the combination of multiple passages in one single-use connection device with a fastening section that comprises a fastening structure on an outer circumferential surface combines multiple advantages simultaneously. The fastening structure serves for the fastening of the single-use connection device in the connection opening of the top plate of the bioreactor and/or in the connection opening of the pouch bioreactor and thus permits the reliable, sealed, quick and simple installation of multiple passages on the bioreactor. By designing different variants of single-use connection devices, it is thus made possible firstly to equip reusable bioreactors with different connections for different applications, wherein cumbersome sterilization processes can be eliminated, and secondly also to provide single-use bioreactors by installing different single-use connection devices easily and inexpensively for different applications. The combination of multiple passages in the single-use connection device furthermore makes it possible for the other components of single-use bioreactors to be manufactured with the fewest possible variants, and thus to further lower costs. Through the formation of a suitable fastening structure on the outer surface on the fastening section, it is furthermore possible—in particular depending on use with single-use or reusable bioreactors—for a non-detachable or a detachable fastening in the connection opening of the top plate or of the connection element to be provided.

The fastening structure can ensure the fastening by means of different technical solutions. Provision is made preferably of a rib structure, a snap-action finger structure, a detent connection, a clip connection, and/or an external thread. The fastening structure may also be realized in the form of an outer diameter of the fastening section dimensioned such that a clamping connection or an interference fit of the single-use connection device in the connection opening is realized. The connection opening is designed to enter into a detachable or non-detachable connection with one or more of the abovementioned fastening structures. For example, in the case of an external thread on the single-use connection device, the connection opening likewise has a thread in order to realize a screw connection. It is preferably possible for sealant and/or seal devices to additionally be incorporated in the fastening section.

The invention is furthermore based on the realization that a single-use connection device of single-piece and/or single-part form offers numerous advantages. For example, the relatively low number of parting joints in the case of the single-piece form is advantageous. Furthermore, the tolerance requirements are reduced, because transmission of tolerances means that smaller deviations from the setpoint dimension have to be ensured. Thus, the single-part design of a connection device can also lead to lower costs. Furthermore, the risk of errors during installation of the connection device is reduced.

According to the invention, the single-use connection device is formed in one piece. "In one piece" means that the single-use connection device is composed only of a single component. The discussed features of the single-use connection device are accordingly formed entirely in a single component, such that no assembly or installation of multiple individual components is necessary.

The invention is furthermore based on the realization that the formation of a connection device from plastic is advantageous with regard to the material characteristics. With the selection of a suitable plastic, it is possible to utilize the chemical resistance of the plastic that exists in particular with respect to chlorinated solutions. Furthermore, a pairing of plastic, for the connection device, and metal and/or glass, for the top plate, contributes to the hermetic sealing of the connection opening, because the thermal expansion of plastic is greater than the thermal expansion of steel or glass. If the top plate and/or the connection element are also composed of plastic or have plastic, it is preferable for the same plastic, or a plastic that exhibits greater thermal expansion, to be used for the single-use connection device. According to the invention, the single-use connection device is therefore formed from a plastic. For the single-use connection device, plastics are preferably selected which meet the requirements of United States Pharmacopoeia (USP) Class VI.

The formation of the single-use connection device from plastic is furthermore advantageous owing to the possibility for one passage or multiple or all passages to be closed off by heat welding and/or hot adhesive bonding and/or other suitable methods. Furthermore, the use of a single-use connection device composed of plastic is advantageous with the use of pouch bioreactors because the risk of damage to the pouch bioreactor, so-called bag damage, can be reduced. Further advantages arise from a production aspect.

With corresponding design, plastics parts can be produced in one piece in an injection molding process. The method permits inexpensive production in a mass production context while ensuring very narrow tolerances. Furthermore, multi-component injection molding allows further elements, such as for example seals, to be molded on. In particular, multi-component injection molding permits the production of a single-piece component with regions having different material characteristics. It is furthermore preferably possible for elements, such as for example a Luer lock system, to be molded directly onto the single-use connection device, or to be provided directly on the single-piece single-use connection device.

A further advantage of the single-use connection device formed from plastic is the possibility for hoses and further elements which are to be connected to be easily fitted onto the passages or onto the walls of the passages. A surface structuring of the outer surfaces of the walls surrounding the passages in accordance with requirements is furthermore possible.

In a preferred design variant, the single-use connection device is characterized in that the fastening structure is in the form of an external thread. In this design variant, the fastening section with the fastening structure preferably has a circular cross section. In this context, the cross section is to be understood as being a cross section orthogonal with respect to a central axis of the fastening section. It is preferable if, on the inner circumferential surface of the connection opening of the top plate or of the connection element, there is formed a complementary fastening structure in the form of a complementary internal thread into which the external thread can engage. In this embodiment, the single-use connection device is preferably detachably fastenable.

In this preferred design variant, the fastening section has, preferably on an outwardly directed surface of its wall, windings which form the abovementioned external thread. The external thread preferably has between 4 and 10 windings, and particularly preferably between 6 and 8 windings. Here, a winding runs all the way around the outwardly directed surface of the fastening section, wherein the start and the end of a winding are spaced apart with regard to a direction parallel to the longitudinal axis of the single-use connection device. The spiral that is thus formed preferably has a longitudinal axis which runs parallel to and congruently with the longitudinal axis of the single-use connection device.

It is preferable for sealant and/or seal devices to additionally be incorporated in the fastening section and/or on the external thread. These may for example be elastic solid bodies, such as sealing bands, and/or pastes and/or gels and/or liquid seals. Here, the sealant and/or seal devices preferably fill the intermediate spaces in the thread and realize a sealing action dependent on the selected sealant and/or seal devices. It is furthermore preferable for the external thread to have a screw locking means which prevents the inadvertent release of the screw connection.

In a particularly preferred design variant, the single-use connection device is characterized in that the fastening structure is realized in the form of ribs, projections, snap-action elements, detent elements, and/or depressions.

Ribs, projections, snap-action elements, detent elements, and/or depressions are fastening structures which can be produced inexpensively, wherein, furthermore, the insertion of the single-use connection device into a connection opening involves little expenditure of time. The ribs, projections, snap-action elements, detent elements, and/or depressions are preferably integrally connected to the single-use connection device. The ribs, projections, snap-action elements, detent elements, and/or depressions may be provided individually or in combination in and/or on the fastening section.

Depending on the fastening structure, it may furthermore be necessary to provide a corresponding geometry in and/or on the connection opening, in particular on the inner circumferential surface thereof, in order to enable, for example, a detent element to engage with detent action. In this embodiment, the single-use connection device may preferably be of detachable or non-detachable form. Furthermore, the ribs, projections, snap-action elements, detent elements, and/or depressions may comprise sealant and/or seal devices for preferably hermetically sealing off the parting joint between the single-use connection device and connection opening.

In a further preferred design variant, the single-use connection device is characterized in that the fastening section has an encircling stop surface, which extends outward in a radial direction from the outer circumferential surface. The encircling stop surface is preferably integrally connected to the single-use connection device. The outer circumferential surface furthermore preferably begins, in the direction of the longitudinal axis of the single-use connection device, directly at the end of the final winding of the external thread.

The single-use connection device is inserted into the connection opening of a bioreactor or of a pouch bioreactor until a section of the surface of the top plate and the stop surface bear directly against one another. It is furthermore preferable for these to bear against one another only indirectly, because a sealant and/or a seal device is arranged between these.

A further particularly preferred design variant of the single-use connection device provides that the fastening section has a force admission section, which comprises a polygonal profile and which preferably directly adjoins the stop surface. The force admission section is preferably arranged in a section of the single-use connection device which, during intended operation of a bioreactor with the single-use connection device, is situated outside the connection opening and outside the bioreactor. The force admission section is furthermore arranged such that it is accessible by hand and/or by means of a tool.

The force admission section serves for the introduction of a force, preferably of a force in a tangential direction, in order to fasten the single-use connection device in the connection opening of a bioreactor and/or in order to release the fastening of the single-use connection device. The action of force on the force admission section is, according to the invention, improved by virtue of a polygonal profile being provided on the force admission section. The polygonal profile on the fastening section of the single-use connection device has the same function, and a geometrically analogous design, to the polygonal profiles in the case of screw heads and/or nuts, wherein hexagonal or tetragonal heads are preferably used in the case of these. The polygonal profile on the fastening section of the single-use connection device may be preferably formed as a double-flat profile, a tetragonal profile, a hexagonal profile, an octagonal profile, a decagonal profile, a dodecagonal profile, and a tetradecagonal profile. The level of the polygonal profile in the direction of the longitudinal axis of the single-use connection device preferably has a dimension between 2 mm and 10 mm, and particularly preferably between 4 mm and 8 mm.

In a further particularly preferred design variant, the single-use connection device is characterized in that one passage, multiple or all passages are formed at least in sections as a pipe segment, wherein, preferably, one pipe segment, multiple or all pipe segments extend parallel to a central axis of the outer circumferential surface in a first direction from the outer circumferential surface and/or in a second direction from the outer circumferential surface.

In this design variant, one passage, multiple passages or all passages have a circular cross section at least in sections. Having a pipe segment at least in sections means that one passage, multiple passages or all passages have a circular cross section either completely over the entire axial length of the respective passage, or have said circular cross section only in certain sections along the axial length of the respective passage. Sections which do not have a pipe segment may have different geometrically shaped cross sections. In particular, the cross sections of the one and/or more passages may be of slot-like, triangular, tetragonal or polygonal form. It is furthermore preferably possible for the cross section to also assume an oval shape. The passage direction of the pipe segment or of the pipe segments or of the passage or of the passages is, in this design variant, parallel to the central axis of the outer circumferential surface.

It is preferable for one pipe segment or multiple or all pipe segments to be formed, for example of thin-walled form, such that said pipe segment(s) can be shortened using a cutting tool. A cutting tool may for example be pliers, cutters or a similar laboratory instrument suitable for shortening and/or truncating the pipe segments.

In a further preferred design variant, the single-use connection device is characterized in that one pipe segment, multiple or all pipe segments have one or more predetermined breaking points. Predetermined breaking points are generally intended to fail in a targeted and predictable manner in an overload situation in order to thereby prevent damage to an overall system. This principle is utilized in the case of the single-use connection device to define predetermined points on the pipe segments at which a user can, by hand, truncate and/or shorten the pipe segments to predetermined lengths, preferably without tools but rather merely by corresponding deformation such as bending and/or breaking.

The predetermined breaking points are therefore designed, by means of structural, mechanical or physical measures, such that, in the event of suitable introduction of force, the pipe segment is severed at a predetermined breaking point. The shortening of the pipe segments can thus be performed without great effort. Furthermore, owing to the low expenditure of force that is required, the risk of damage to the single-use connection device, for example to the integrity, is reduced. The predetermined breaking points are preferably formed as notches.

A further preferred design variant of the single-use connection device provides for one pipe segment, multiple or all pipe segments to be at least deformable under the action of heat such that the respective passage is closable in fluid-tight fashion as a result of a change in shape. The action of heat is preferably realized by means of heat welding, hot adhesive bonding or the like. The deformability of the pipe segments is determined in particular through the selection of the material of the pipe segments. Here, provision is preferably made of a thermoplastic material, such that one pipe segment or multiple or all pipe segments are formed from a meltable plastic. By the action of heat and the subsequent deformation of the pipe segment or of the pipe segments, the passage is closed off in fluid-tight fashion. "Closed off in fluid-tight fashion" means that, through the passage that has been closed off in fluid-tight fashion, no fluid can flow, or pass in any other way, from a first end of the passage to a second end of the passage.

This design variant increases the practicability of the single-use connection device, because the latter is more universally usable. If a required number of passages is smaller than the number of available passages on the single-use connection device, it is possible for the user to close off one or more passages. As a result, only the number of passages that is actually required are present. For the user, this simplifies the use, because the user has no need to stock a large number of different connection devices, and the risk of confusion is additionally reduced. Furthermore, the purchase costs can be reduced through economies of scale.

In a further particularly preferred design variant, the single-use connection device is characterized in that one pipe segment, multiple or all pipe segments are closed off at at least one end by means of a hose-securing device.

For a successful cultivation of microorganisms and/or cell cultures, it is important for the influential factors in the bioreactor, for example temperature, nutrient supply, pH value, oxygen content, homogenization and/or foam formation, to lie at a value or in value range defined by the user.

A reliable feed and/or discharge of media is important in order to keep the stated influential factors in the bioreactor in the defined value range. The feeds and discharges are ensured through the passages in the single-use connection device and through hoses connected to said passages. A reliable feed and discharge of media is ensured, inter alia, by means of hose-securing devices which prevent an inadmissible or inadvertent removal of the hoses that are connected to the passages in the single-use connection device. The hose-securing device is preferably formed as a Luer lock system.

In a further design variant, at least one pipe segment is formed from plastic and has a filter element at an end provided for insertion into the bioreactor.

The end provided for insertion into the bioreactor is also referred to as inner end. Through the use of a filter element or filter, it can firstly be ensured that no cells from the culture broth exit the bioreactor in the case of the respective pipe segment being used for a discharge of media, because said cells are retained by the filter. The use of a filter is however also advantageous in pipe segments for the supply of media or gases; by means of the porous structure of the filter, the supplied medium or the gas is conducted in finely distributed fashion into the culture broth. It is therefore advantageous in particular if the pipe segment that has the filter element is designed to be long enough that, when inserted into the bioreactor, the end of the pipe segment and in particular also the filter element are arranged in the culture broth.

Depending on the usage situation, the filter element preferably has a pore size in a range from 0.1 μm-500 μm, in particular in a range from 0.1-0.2 μm, from 0.1 to 1 μm, from 0.5-5 μm, from 5-50 μm, from 5-250 μm, from 20-40 μm, from 20-100 μm, from 20-250 μm or from 5-500 μm.

The pore size may preferably be understood to mean a nominal pore size, that is to say a maximum of the pore size distribution. In further embodiments, the pore size may be understood to mean that the filter element has exclusively pores whose pore size lies within the stated value ranges. The determination of the pore sizes may be determined by mercury intrusion as described in DIN66133 of June 1993. DIN66133 can be obtained from Beuth-Verlag, Am DIN-Platz, Burggrafenstraß6, 10787 Berlin.

In one design variant, the filter element projects beyond the end of the pipe segment, such that said filter element can be surrounded over a large area by the medium. In an alternative embodiment, the filter element terminates flush with the end of the pipe segment or is slightly set back in relation thereto. In this embodiment, the medium impinges predominantly on the end face of the filter element.

The filter element may comprise a diaphragm and/or have a porous structure. In particular, the filter element may comprise or be composed of a glass filter, a porous ceramic, in particular a foamed ceramic, a plastics filter or a filter cassette. The filter element preferably comprises borosilicate, aluminum oxide, zirconium oxide, polycarbonate, polypropylene, and/or polyethylene. A glass filter may preferably be composed of borosilicate or comprise borosilicate. A porous ceramic may preferably be composed of aluminum oxide and/or zirconium oxide or comprise aluminum oxide and/or zirconium oxide. A plastics filter may preferably be composed of polycarbonate and/or polypropylene and/or polyethylene and/or comprise polycarbonate and/or polypropylene and/or polyethylene. A filter cassette may preferably be filled, for example with diatomaceous earth and/or fibers and/or other materials.

The filter element may preferably be modified and/or aftertreated, in particular coated and/or activated, in particular such that a surface of the filter element is hydrophobic or hydrophilic.

The plastic of the at least one pipe segment is preferably a thermoplastic.

For the filter element and/or the at least one pipe segment, use is preferably made of materials that fall under USP Class VI.

The pipe segment and the filter element are preferably formed integrally by means of hybrid injection molding, in the case of which, firstly, the filter element is injection molded, or produced by some other shaping method, and/or is sintered, and subsequently the pipe segment is injection molded in parts around the prefabricated, possibly already-sintered, filter element. The filter element may for example be adhesively bonded, connected with detent action, welded, or connected by means of an interference fit to the pipe segment.

In a further preferred design variant, the single-use connection device is characterized by one sensor or multiple sensors and/or one electrode or multiple electrodes, wherein, preferably, at least one sensor and/or at least one electrode is arranged in one passage, multiple or all passages. A sensor may comprise one or more electrodes, or may be formed as an electrode. In the case of multiple electrodes being provided, these are preferably spaced apart from one another and/or electrically insulated with respect to one another. The electrode(s) is/are preferably formed as bar electrode(s) or as substantially bar-shaped electrode carrier(s) with electrode (s) fastened thereto.

In a preferred embodiment, the single-use connection device has at least two spaced-apart electrodes which are electrically insulated with respect to one another and which are preferably each arranged in a passage. Alternatively, two or more electrodes and/or sensors may also be arranged together in one passage with a corresponding diameter. If, for example, the electrodes and/or sensors arranged in one passage end at different levels in the passage, and the passage is dimensioned as an immersion pipe, it is also possible within the passage for the fill level, for example, to be detected as described below. Deviations caused by a possible capillary effect can be eliminated or reduced through corresponding calibration and/or dimensioning of the passage.

For example, a sensor may be formed as a fill level sensor which measures the level of the medium situated in the reactor, wherein the level is preferably measured in a vertical direction. The fill level sensor of the single-use connection device may preferably be formed with at least one electrode, preferably two or more electrodes, wherein the measurement is performed above the medium or in the medium. If the fill level sensor of the single-use connection device has only one electrode, it is preferable for at least one further electrode to be arranged at another location on or in the bioreactor, in order that, in particular from the point at which a certain fill level is reached, a voltage can prevail. In particular, in the case of steel-tank bioreactors or bioreactors composed of other conductive materials, it is for example possible for the reactor wall to form a further electrode of said type. The determination of the level is furthermore preferably performed by means of the measurement of a voltage between at least two electrodes.

In a further embodiment, it is also possible for foam formation to be measurable by means of the at least one sensor and/or of the at least one electrode. In this case, the electrical conductivity between the two electrodes is preferably measured, wherein, as described above, the first electrode is preferably arranged on the single-use connection device and the second electrode may be arranged on the bioreactor (for example as a wall of a steel bioreactor) or may likewise be arranged on the single-use connection device. Foam has a different, in particular lower, electrical conductivity in relation to the medium. By means of the measurement of the electrical conductivity and a comparison with reference values for foam and/or medium, it is thus possible for foam formation in the bioreactor to be detected.

In a further embodiment, a single-use connection device according to the invention has a sensor with at least three electrodes, of which a first electrode is formed and arranged as a fill level sensor for the medium, a second electrode is formed and arranged for the measurement of foam formation, and a third electrode is formed and arranged as a common counterpart electrode.

The at least one sensor and/or the at least one electrode may either be inserted into a passage or multiple passages of the single-piece single-use connection device or may be integrally connected to the single-use connection device. The latter variant generally requires an injection molding process, in which the at least one sensor and/or the at least one electrode are or is encapsulated as an insert part. The encapsulation offers the advantage of an integral component which does not have to be installed, and of an intense sealing action between the electrode and the surrounding material of the single-use connection device. Furthermore, the axial position of the at least one sensor and/or of the at least one electrode in the single-use connection device is defined such that, here, there is a reduced risk of errors in the installation process or in the process device.

In a further particularly preferred design variant, the single-use connection device is characterized by an encircling seal for fluid-tight sealing with respect to the bioreactor. The encircling seal is preferably arranged on a section of the encircling stop surface, wherein said section, in the installed state, faces toward the surface of the top plate of the bioreactor and/or the surface of the pouch bioreactor. Sealing of this parting joint has the effect of improving the hermetic sealing of the interior space of the bioreactor. As sealant, use may be made of conventional sealing rings composed of an elastic material and/or of sealing pastes, gels and/or other sealing materials. The encircling seal is furthermore preferably integrally connected to the single-use connection device. This integral design is made possible, for example, by virtue of a seal being molded on in the production process, wherein use is made here in particular of a multi-component injection molding process.

According to a further aspect of the invention, the object stated in the introduction is achieved by means of a top plate for a bioreactor, having a connection opening, wherein the top plate is designed to be fastened to a vessel of the bioreactor, and a connection device inserted or insertable into the connection opening, characterized in that the connection device is designed as per at least one of the above-described embodiments of the single-use connection device.

The bioreactor generally has a fully closed enclosing wall, wherein one side is closed off by a top plate. The top plate has the function of ensuring the complete enclosure of the bioreactor and/or the feed and/or discharge of media and introduction and/or removal of instruments. The top plate is preferably connected to an enclosing wall of the bioreactor, preferably a vessel with a vessel opening. It is furthermore preferable for the top plate to close the partially open enclosing wall of the vessel and/or the vessel opening in order to hermetically seal off the vessel. The connection may be of cohesive and/or non-positively locking and/or positively locking form, in particular in a manner dependent on the material of the top plate and on the material of the vessel. The top plate may be composed of or comprise metallic and/or ceramic materials and/or plastic.

The top plate furthermore has at least one connection opening which serves for the receiving or fastening of the single-use connection device. The connection opening furthermore preferably has a structure which is designed for receiving the fastening structure of the single-use connection device. In the case of the single-use connection device being formed with an external thread, the connection opening preferably has an internal thread.

The top plate furthermore has an areal extent, wherein the areal extent preferably has a substantially horizontal extent in the operating state, that is to say when installed on a vessel of the bioreactor and set up on a substantially horizontal working surface. A thickness measured horizontally with respect to the areal extent has a small dimension in relation to the areal extent. The top plate may preferably have a predominantly planar extent. It is alternatively preferably possible for the top plate to also have a domed extent. The top plate may furthermore also have reinforcement elements, for example rib arrangements.

The single-use connection devices are generally attached in or to the connection openings of the top plate. Said connection openings, in particular during operation of the bioreactor when set up on a substantially horizontal working surface, preferably have a substantially vertical passage direction. The connection openings have a cross section orthogonal with respect to their central axis. Said cross section may preferably be circular, slot-like, triangular, tetragonal, and/or polygonal. The cross section may furthermore preferably also assume an oval shape.

According to a further aspect of the invention, the object stated in the introduction is achieved by means of a bioreactor for cultivating microorganisms and/or cell cultures, having a vessel and a top plate for closing off the vessel, characterized in that the top plate is designed as per the aspect described above.

By means of a bioreactor of said type having a top plate according to the invention and comprising a single-use connection device according to the invention, various disadvantages of existing embodiments of bioreactors can be alleviated or eliminated. By means of the single-use design, the single-piece form and chemical resistance of the single-use connection device, it is the case in particular that the risk of contamination of the bioreactor is reduced. Furthermore, the single-piece form and the possibility of the secure attachment of hoses increase the operational reliability of the bioreactor.

Here, it is particularly advantageous if the connection device comprises at least one pipe segment whose end arranged in the bioreactor is situated below a minimum fill level for culture medium of the bioreactor. The pipe segment preferably comprises the filter element. It may therefore also suffice for only the filter element or the end thereof—the lower end in the operating state—to be situated below the minimum fill level. It is thereby ensured that the pipe segment projects into the culture medium regardless of the actual fill level in the bioreactor. In this embodiment, it is important that the pipe segment is designed so as to project into the culture medium. It is thus possible for gassing of the culture medium to be performed via the pipe segment, in the case of which air or else other gases can be introduced directly into the culture medium. Alternatively, the pipe segment may be utilized to extract culture medium or products of the cells contained in the culture medium. It is thus possible to realize both an exchange of media and a recovery of products. In particular, it is advantageous if the respective pipe segment serves alternately for gassing and for extraction, because then back-flushing at the pipe segment is performed, and contamination of the pipe segment, for example, with remaining residues of medium, is avoided. Here, it is particularly advantageous if the pipe segment, as already described, has a filter element. This can, depending on the usage situation, ensure fine-bubble gassing and prevent undesired extraction, for example of the cells in the culture medium.

According to a further aspect of the invention, the object stated in the introduction is achieved by means of a connection element for a pouch bioreactor, having a connection opening, wherein the connection element is designed to be connected to, and/or to be formed in one piece with, a pouch vessel, and a connection device inserted or insertable into the connection opening, characterized in that the connection device is designed as per at least one of the above-described embodiments of the single-use connection device.

According to a further aspect of the invention, the object stated in the introduction is achieved by means of a pouch bioreactor for cultivating microorganisms and/or cell cultures, having a deformable pouch vessel with a connection element, characterized in that the connection element is designed as per the aspect described above.

In this case, too, it is advantageous if the connection device of the connection element comprises at least one pipe segment whose end arranged in the pouch bioreactor is situated below a minimum fill level for culture medium of the pouch bioreactor.

For further advantages, design variants and design details of these further aspects and the possible developments thereof, reference is also made to the above description relating to the corresponding features and developments of the single-use connection device.

BRIEF DESCRIPTION OF THE DRAWINGS

Preferred embodiments of the invention will be discussed by way of example on the basis of the appended figures, in which:

FIG. 3b shows a longitudinally sectioned sectional illustration of a possible variant of the single-use connection device according to FIG. 1;

FIG. 7a shows a schematic illustration of a bioreactor with top plate;

FIG. 7b shows a schematic illustration of a pouch bioreactor with connection element.

DETAILED DESCRIPTION OF THE EMBODIMENTS

In the Figures, the same or corresponding elements or units are each provided with the same and/or the corresponding reference signs. When an element or a unit has already been described with reference to a particular Figure, a detailed description is dispensed with when discussing another Figure. However, it is to be understood that the present disclosure may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale.

Figure 1:
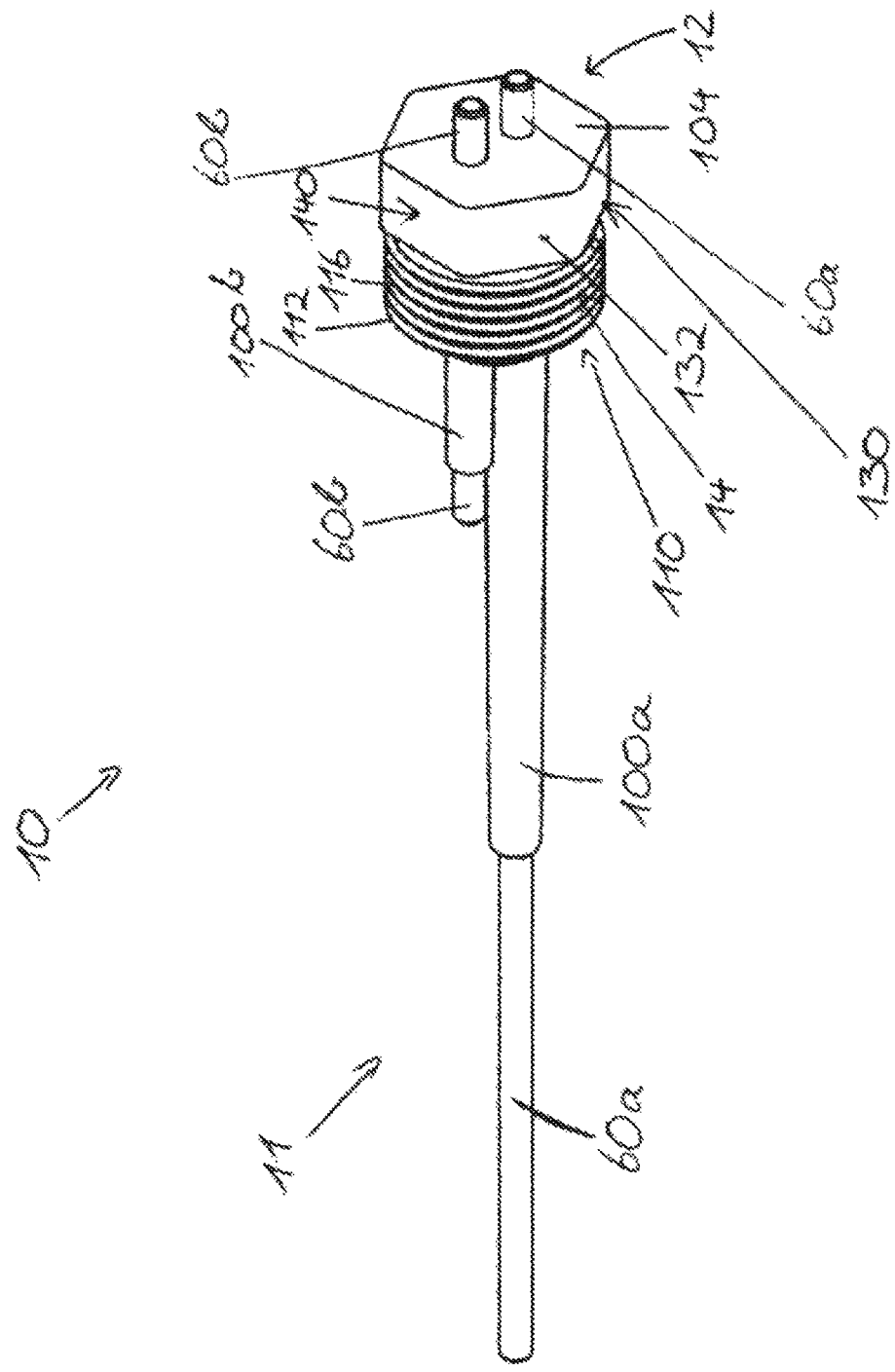
FIG. 1 shows a three-dimensional illustration of a first exemplary single-use connection device.

FIG. 1 shows a three-dimensional illustration of a first exemplary embodiment of a single-use connection device 10, having a first sensor 60a formed as a fill level sensor and having a second sensor 60b formed as a fill level sensor. The single-use connection device 10 comprises an outer end 12, at which a delimiting disk 104 is arranged. The delimiting disk 104 covers an end side of a force admission section 130 formed as a sleeve, wherein the end side covered by the delimiting disk 104 faces toward the outer end 12. The force admission section 130 formed as a sleeve has an outer circumferential surface. Said outer circumferential surface of the force admission section 130 has a polygonal profile 140, which is formed in this case as a hexagonal profile. The polygonal profile 140 is composed of six planar surfaces 142 of equal size, which are distributed uniformly on the outer circumferential surface of the force admission section 130. The individual surfaces 142 are arranged such that the respective surface normal thereof runs through the central axis of a sleeve 14, and in each case two edges of an individual surface in turn adjoin in each case one edge of two further surfaces.

In a longitudinal direction in the direction of the inner end 11, there is arranged on the force admission section 130 a fastening section 110 which has the same central axis as the force admission section 130. The fastening section 110 is likewise formed as a sleeve with a constant diameter, wherein the diameter of the fastening section 110 is smaller than the diameter of the force admission section 130. There is thus a step or a shoulder at the transition from the force receiving section 130 to the fastening section 110. Said shoulder serves as a stop surface 120, as perhaps best shown in FIG. 2, such that the single-use connection device 10 is inserted, as far as this transition, into a connection opening of a bioreactor. Furthermore, the fastening section 110 has an outer circumferential surface 112, on which there is formed an external thread 116.

A first inner pipe section 100a and a second inner pipe section 100b, each with a passage direction in the direction of the inner end 11, emerge from the sleeve that forms the fastening section 110. The projecting lengths, in relation to the emergence from the fastening section 110, of the two inner pipe sections 100a, 100b differ, wherein the first inner pipe section 100a has a projecting length approximately three times that of the second inner pipe section 100b. Furthermore, FIG. 1 shows a first fill level sensor 60a and a second fill level sensor 60b, which in this case are formed as bar electrodes. The two fill level sensors 60a, 60b have substantially the task of measuring the vertical level of a medium situated in the bioreactor and transmitting said value in a suitable form to a further device. Here, the one fill level sensor is substantially designed to detect the upper fill level, and the respective other fill level sensor is substantially designed to detect the lower fill level.

The two fill level sensors 60a, 60b may also serve for measuring foam formation. In this case, it is preferable for the electrical conductivity between the two electrodes to be measured, wherein foam is distinguished by a lower electrical conductivity in comparison to the medium, and thus foam formation in the bioreactor can be detected.

The fill level sensor 60a is arranged with a part of its longitudinal extent in the passage of the first inner pipe section 100a. The fill level sensor 60a may either be inserted into the passage or may already be encapsulated in the production process of the single-use connection device 10. The arrangement and introduction of the first fill level sensor 60a applies analogously to the arrangement and introduction of the second fill level sensor 60b in the passage of the second inner pipe section 100b. The passages of the inner pipe segments 100a, 100b preferably extend as far as the outer end 12, such that the delimiting disk 104 has two passage openings. It is furthermore preferable for the fill level sensors 60a, 60b to emerge in each case with one end out of the single-use connection device 10, such that, for example, it is made possible for the fill level sensors 60a, 60b to be connected to further devices.

Figure 2:
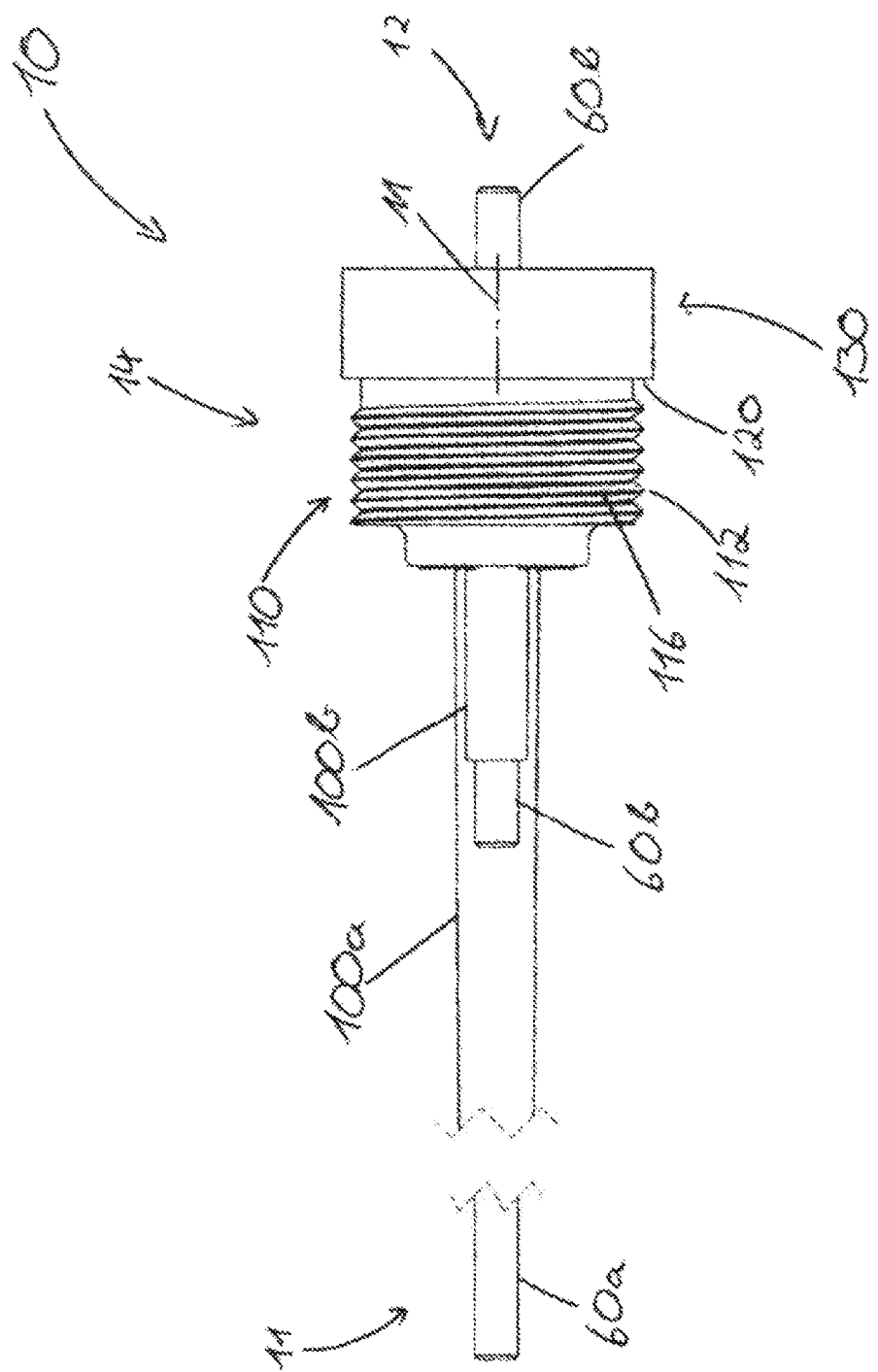
FIG. 2 shows a side view of the single-use connection device according to FIG. 1.

FIG. 2 shows a side view of the single-use connection device as per FIG. 1, with a first fill level sensor 60a and a second fill level sensor 60b. At the outer end 12 of the single-use connection device 10, in each case one end of a first fill level sensor 60a and of a second fill level sensor 60b emerges from the single-use connection device 10. The end of the first fill level sensor 60a at the outer end 12 is concealed in FIG. 2 by the end of the second fill level sensor 60b, such that the former is not shown. The ends of the fill level sensors 60a, 60b accordingly project, at the outer end 12, out of a sleeve 14, which comprises a force admission section 130, a stop surface 120, and a fastening section 110. The sleeve furthermore has a central axis M, which is likewise the central axis of the force admission section 130 and of the fastening section 110.

The force admission section 130 is formed as a sleeve, wherein the fastening section 110 is arranged on the force admission section 130 in the direction of the inner end 11. The fastening section is likewise formed as a sleeve, wherein the diameter of the fastening section 110 is smaller than the diameter of the force admission section 130. As a result of this diameter difference, there is a shoulder at the transition from the fastening section 110 to the force admission section 130, by means of which shoulder a surface is formed, the surface normal of which is oriented orthogonally with respect to the central axis M. Said surface serves as the stop surface 120, such that the single-use connection device 10, when inserted into a connection opening of a bioreactor, is inserted into the connection opening as far as said stop surface 120. The force admission section 130 preferably remains entirely outside the connection opening.

The fastening section 110 has an outer circumferential surface 112, on which an integrally formed fastening structure 114 is arranged. The fastening structure 114 is formed in this exemplary embodiment as an external thread 116, which has a number of windings. The two inner pipe segments 100a, 100b are arranged parallel to the central axis M. Furthermore, the two inner pipe segments 100a, 100b emerge from the sleeve on the side of the inner end and each have different projecting lengths. In each case one of the fill level sensors 60a, 60b emerges at that end of the two inner pipe segments 100a, 100b which is directed towards the outer end 12 of the single-use connection device.

Figure 3A:
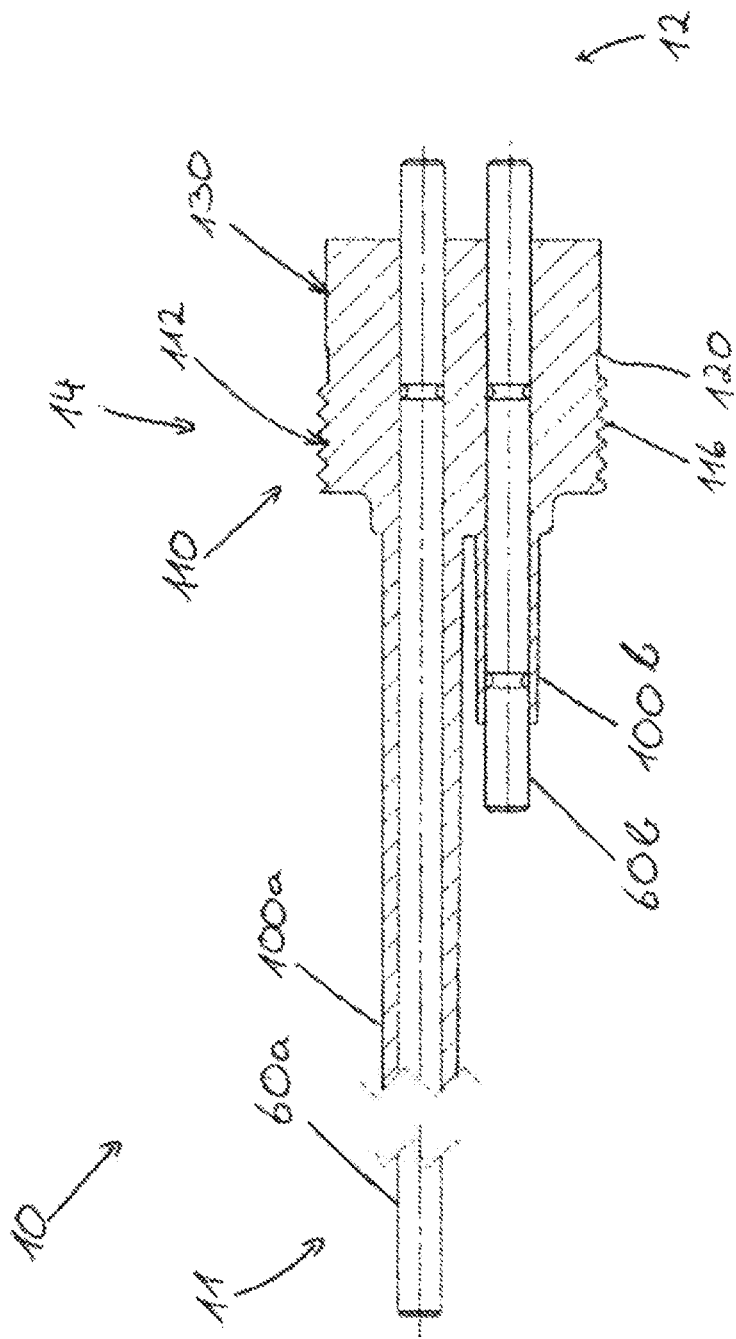
FIG. 3a shows a longitudinally sectioned sectional illustration of the single-use connection device according to FIG. 1.

FIG. 3a shows a longitudinally sectioned sectional illustration of a single-use connection device as shown in FIG. 1. The single-use connection device 10 extends from an outer end 12 to an inner end 11. A first fill level sensor 60a and a second fill level sensor 60b emerge from the single-use connection device 10 in a longitudinal direction at the outer end 12. The fill level sensors 60a, 60b are, analogously to the Figure descriptions given above, designed as bar electrodes. The outer end 12 of the single-use connection device 10 is formed by a force admission section 130, which is designed to admit an externally applied force with which, for example, the single-use connection device 10 can be inserted into a connection device.

In a longitudinal direction in the direction of the inner end 11, a fastening section 110 is arranged on the force admission section 130. The fastening section 110 is formed by an outer circumferential surface 112, wherein the latter has a smaller diameter than the force admission section 130. By means of this diameter difference, there is formed a shoulder at the transition from the force admission section 130 to the fastening section 110. A surface thus formed has a surface normally oriented parallel to a central axis of the force admission section 130 and of the fastening section 110. The stop surface 120 thus formed serves for the insertion of the single-use connection device 10 into a connection opening of a bioreactor. Here, the stop surface 120 lies on a surface which is situated in the direct vicinity of the connection opening.

The fastening section 110 has, on the outer circumferential surface 112, a fastening structure 114 which, in the present exemplary embodiment, is formed as an external thread 116. On that end side of the fastening section 110 which faces toward the inner end 11, there are arranged two inner pipe segments 100a. Central axes of said two inner pipe segments 100a are parallel to the central axis of the force admission section 130 and of the fastening section 110. The labelled fill level sensors 60a, 60b emerge at those ends of the first inner pipe segment 100a and of the second inner pipe segment 100b which are directed toward the outer end 12 of the single-use connection device. The fill level sensors 60a, 60b accordingly extend all the way from the outer end 12 to the inner end 11 of the single-use connection device 10. The fill level sensors 60a, 60b are, for this purpose, in each case inserted into passages or encapsulated already during the production process, wherein the passages lead in each case with a common central axis through the pipe segments 100a, the fastening section 110 and the force admission section 130.

FIG. 3b shows a longitudinally sectioned sectional illustration of a possible variant of the single-use connection device 10 shown in FIG. 1, wherein the single-use connection device 10 in this case, by contrast to the variant in FIG. 3a, has a cavity in the region of a force admission section 130 and in the region of the fastening section 110. The cavity is surrounded by an enclosing wall in a radial direction from a central axis M, wherein the outer surface of said enclosing wall comprises an external thread 116 in the region of the fastening section 110.

In the installed state of the single-use connection device 10, the delimiting disk 104 separates the interior space of a bioreactor from the surroundings of the bioreactor. On that side of the delimiting disk 104 which faces toward the outer end 12, there are arranged a first outer pipe segment 101a and a second outer pipe segment 101b. The first outer pipe segment 101a has the same passage as the first inner pipe segment 100a. Furthermore, the second outer pipe segment 101b has the same passage as the second inner pipe segment 100b. To ensure the delimitation-free passage from an inner pipe segment to an outer pipe segment, the delimiting disk 104 has passage holes, the passage direction and central axis of which in each case identically corresponds to the passage direction and the central axis of the pipe segments arranged at said passage holes.

Figure 4:
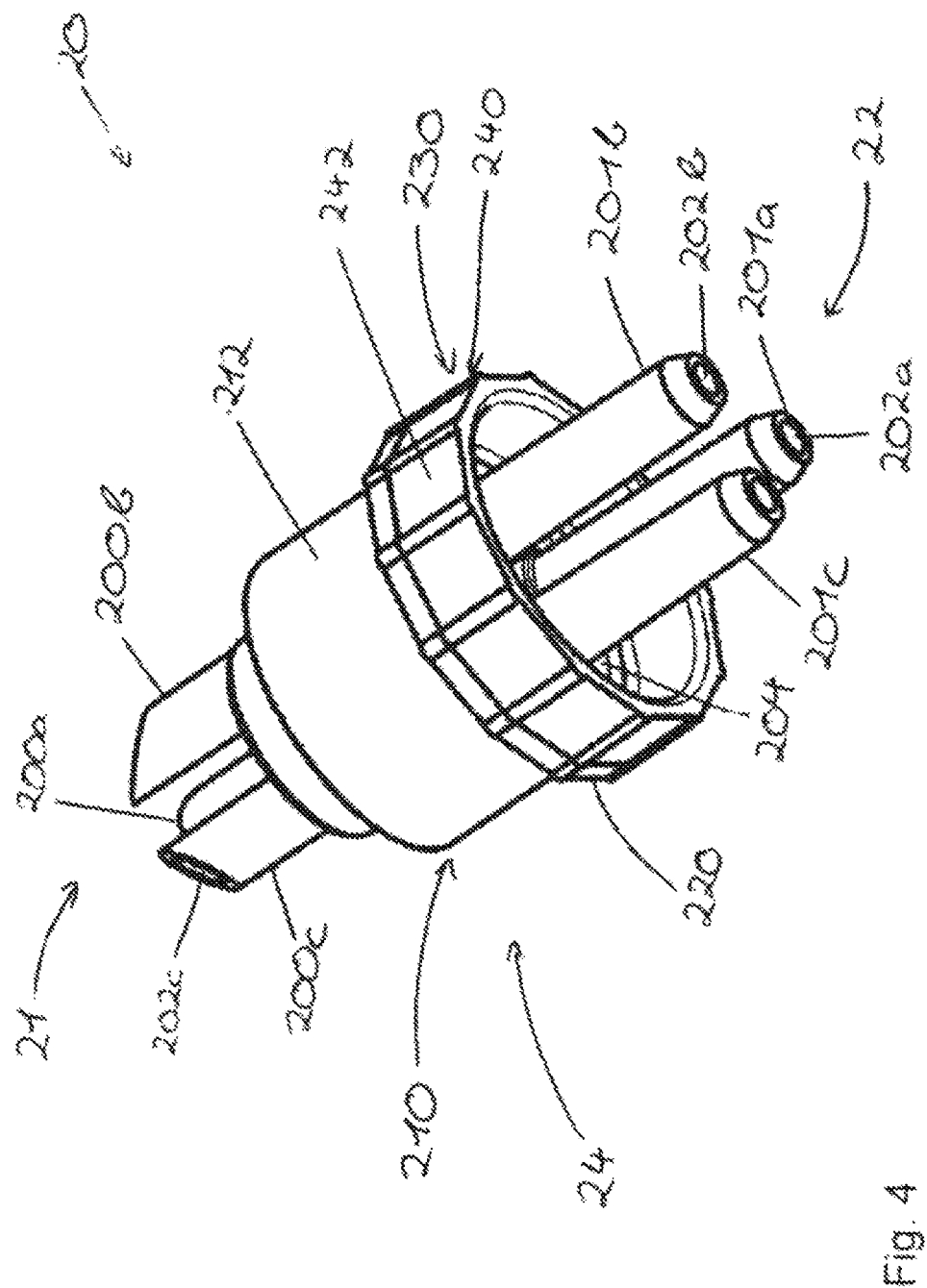
FIG. 4 shows a three-dimensional illustration of a second exemplary single-use connection device.

FIG. 4 shows a three-dimensional illustration of a second exemplary embodiment of a single-use connection device 20. The single-use connection device 20 has an inner end 21 and an outer end 22. The inner end 21 of the single-use connection device 20 is the end that is introduced and/or inserted into a connection opening of a bioreactor. The inner end 21 accordingly, in the inserted state, faces toward the interior space of the bioreactor. In this exemplary embodiment, the inner end 21 comprises a first inner pipe segment 200a, a second inner pipe segment 200b and a third inner pipe segment 200c. The inner pipe segments 200a, 200b, 200c each have the same axial length and furthermore also the same projecting length in relation to a delimiting disk 204. The delimiting disk 204 has an areal geometry, the surface normal of which runs parallel to the passage direction of the pipe segments. The inner pipe segments 200a, 200b, 200c each have a passage 202a, 202b, 202c. The three inner pipe segments 200a, 200b, 200c are furthermore in each case spaced apart from one another in a radial direction.

The outer end 22 is the end that is not introduced and/or inserted into the connection opening of the bioreactor. The outer end 22 is accordingly, in the inserted state, averted from the interior space of the bioreactor. The outer end 22 comprises three outer pipe segments 201a, 201b, 201c, which each have the same axial length and are spaced apart from one another in a radial direction. Furthermore, in this design variant, the three outer pipe segments have the same projecting length in relation to the delimiting disk 204.

The outer pipe segments 201a, 201b, 201c likewise each comprise the passages 202a, 202b, 202c. Each individual passage 202a, 202b, 202c runs all the way through the single-use connection device, such that a passage 202a, 202b, 202c begins at the inner end 21, in an inner pipe segment 200a, 200b, 200c, and runs preferably in uninterrupted fashion to the outer end 22, in an outer pipe segment 201a, 201b, 201c. The passage 202a is accordingly formed predominantly by the first inner pipe segment 200a and the first outer pipe segment 201a. The passage 202b is furthermore formed predominantly by the second inner pipe segment 200b and the second outer pipe segment 201b. The passage 202c is furthermore predominantly formed by the third inner pipe segment 200c and the third outer pipe segment 201c.

An individual inner pipe segment 200a, 200b, 200c and a corresponding individual outer pipe segment 201a, 201b, 201c accordingly have a common central axis. An inner pipe segment 200a, 200b, 200c and a corresponding outer pipe segment 201a, 201b, 201c with common central axis are held in a defined position by the circular delimiting disk 204 arranged orthogonally with respect to the central axis. The circular disk 204 has passage openings, such that the passages 202a, 202b, 202c are continuous from the inner end 21 to the outer end 22. The ends of the inner pipe segments 200a, 200b, 200c each have an end face which is inclined at approximately 45 degrees with respect to the central axis of the pipe segment. The wall thickness of the outer pipe segments 201a, 201b, 201c decreases toward the outer end, wherein the wall thickness is approximately halved.

The inner and outer pipe segments and the delimiting disk 204 are surrounded in a radial direction by a sleeve 24 which has a fastening section 210, a stop surface 220, and a force admission section 230. The fastening section 210 has an outer circumferential surface 212. The outer circumferential surface 212 furthermore has a substantially constant diameter. A fastening structure 214 is in this case realized in the form of an outer diameter of the fastening section 210 dimensioned, such that a clamping connection or interference fit of the single-use connection device 20 in a connection opening is realized. The force admission section 230 is arranged directly on that end of the fastening section 210 which faces toward the outer end 22. The force admission section 230 has a circular inner diameter larger than the inner diameter of the fastening section 210.

The outer circumferential surface of the force admission section 230 has a dodecagonal profile 240. The dodecagonal profile 240 is composed of twelve planar surfaces 242 of equal size, which are distributed uniformly on the outer circumferential surface of the force admission section 230. The individual surfaces 142 are arranged such that the respective surface normal thereof runs through the central axis of the sleeve 24 and in each case two opposite edges of an individual surface in turn adjoin in each case one edge of two further surfaces.

By virtue of the fact that the force admission section 230 has a larger diameter than the fastening section 210, a shoulder or a step is formed at the transition from the fastening section 210 to the force admission section 230, which shoulder or step is oriented orthogonally with respect to the surface of the fastening section 210. A connection opening of a bioreactor is preferably designed such that the diameter of the connection opening has an identical or a smaller dimension than the diameter of the fastening section 210. Furthermore, the diameter of the connection opening is smaller than the diameter of the force admission section 230, such that the abovementioned step acts as a stop surface 220. After the insertion of the single-use connection device 20, the stop surface 220 lies on the surface of that element of the bioreactor which has the connection opening.

Figure 5:
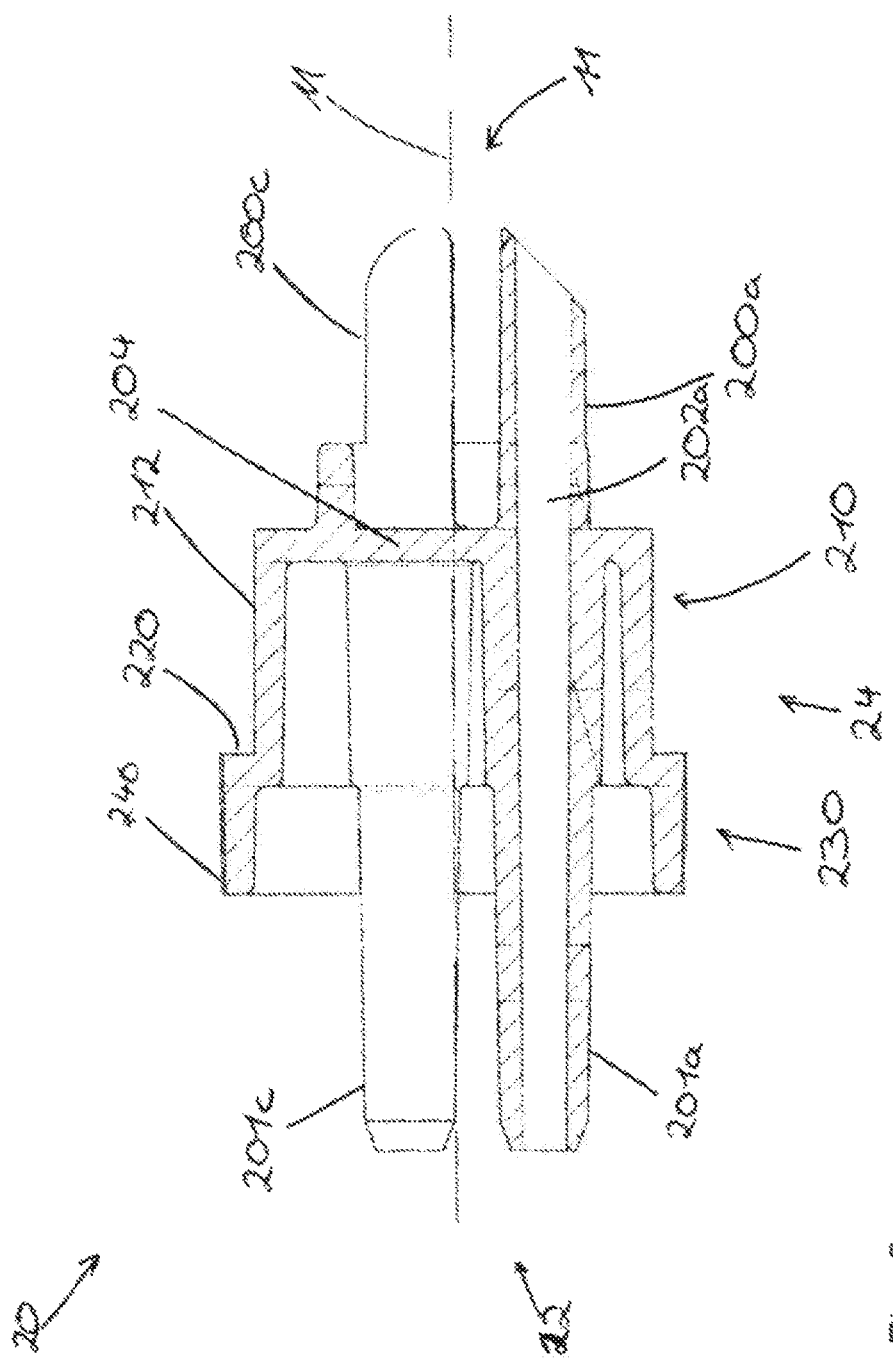
FIG. 5 shows a longitudinally sectioned sectional illustration of a single-use connection device according to FIG. 4.

FIG. 5 shows a longitudinally sectioned sectional illustration of a design variant of the single-use connection device as shown in FIG. 4. The single-use connection device 20 has, on the outer end 22, a total of three outer pipe segments, wherein the pipe segment 201b is arranged outside the section plane and the pipe segment 201c is illustrated in a non-sectional perspective view, because it is situated behind the section plane. The single-use connection device 20 furthermore has a sleeve 24 which comprises the force admission section 230, the stop surface 220 and the fastening section 210.

The fastening section 210 has a rotationally symmetrical form with respect to the central axis M, such that the fastening section 210 likewise has the form of a sleeve. Furthermore, the fastening section 210 comprises an outer circumferential surface 212, on which a fastening structure (not illustrated) may be formed. On that end side of the fastening section 210 which faces toward the inner end 21, there is situated a delimiting disk 204 which substantially completely closes off the end side of the fastening section 210. The delimiting disk 204 therefore has a surface normal which is oriented parallel to the central axis M.

Considering FIGS. 4 and 5, the outer pipe segments 201a, 201b, 201c and the inner pipe segments 200a, 200b, 200c are also arranged on the delimiting disk 204. Here, in each case one outer pipe segment and one inner pipe segment form a common passage 202a, 202b, 202c. At the point at which an outer pipe segment and an inner pipe segment are arranged on the delimiting disk 204, a passage opening is likewise situated in the delimiting disk 204, such that each of the three passages 202a, 202b, 202c is continuous from the inner end 21 to the outer end 22.

Figure 6:
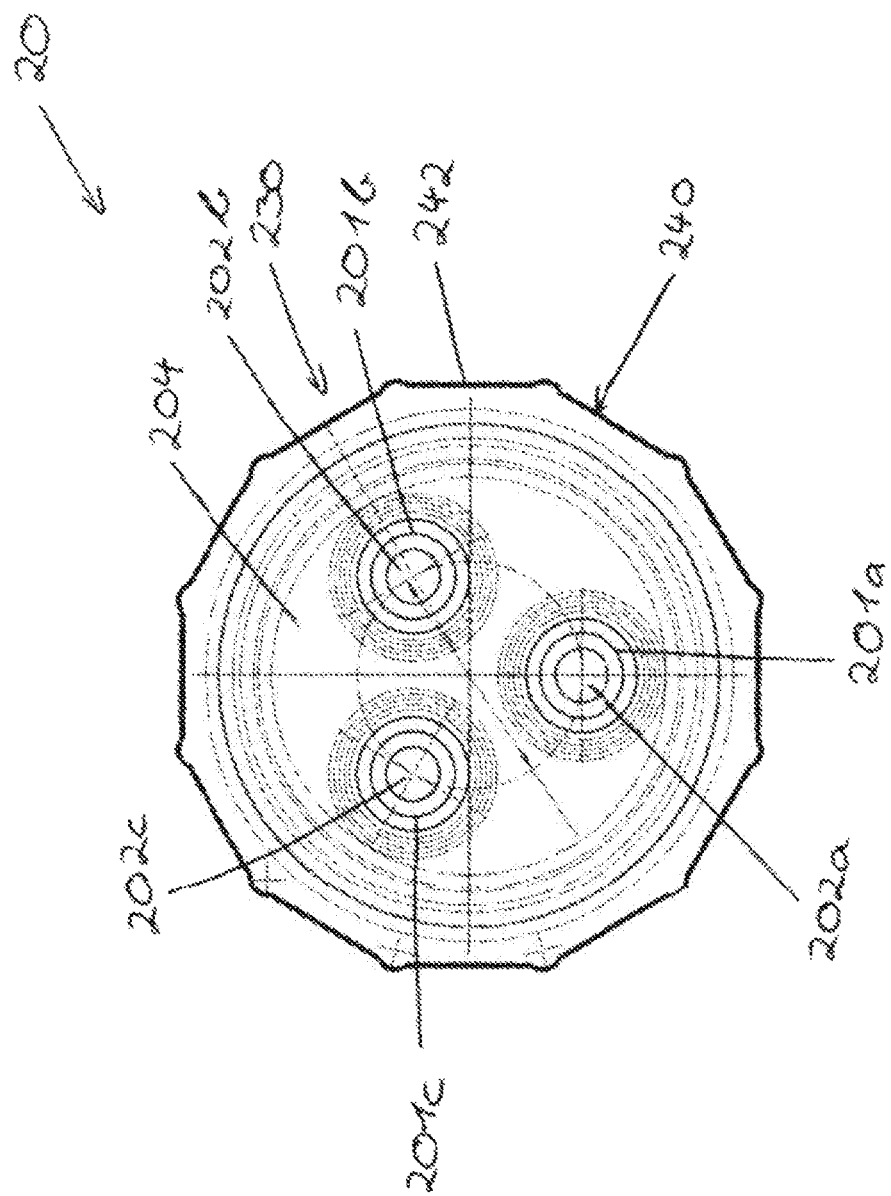
FIG. 6 shows a plan view of the single-use connection device according to FIG. 4.

FIG. 6 shows a plan view of the single-use connection device 20 as per FIG. 4. Three outer pipe segments 201a, 201b, 201c are arranged on the delimiting disk 204. The outer pipe segments 201a, 201b, 201c furthermore have a circular cross section, wherein the central points thereof each have the same spacing to the central point of the delimiting disk 204. Furthermore, the three outer pipe segments have the abovementioned passages 202a, 202b, 202c. The single-use connection device 20 furthermore comprises a force admission section 230, which is designed to be acted on with a radial and/or axial force in order to fasten the single-use connection device 20 preferably in an/or on a connection opening of a bioreactor. The force admission section 230 therefore has the polygonal profile already described above, which is in this case composed substantially of twelve polygonal-profile surfaces 242.

FIG. 7a shows a schematic illustration of a bioreactor 50 with top plate 40. The bioreactor 50 comprises a bioreactor vessel 51, which is preferably fully enclosed by walls with the exception of one side. The vessel is preferably formed from a metallic material, preferably rust-resistant steel, and/or plastic, or comprises said materials. That side of the bioreactor vessel 51 which is not enclosed by a wall is closed off by a top plate 40. The top plate furthermore has a connection opening 30 which is designed to receive a single-use connection device 10, 20 according to the invention. The connection opening 30 preferably has, on its inner circumferential surface, an internal thread which enables an external thread of complementary form on a single-use connection device 10, 20 to be received.

FIG. 7b shows a schematic illustration of a pouch bioreactor 55 with a connection element 45 and with a pouch 56 which is substantially, or at least in sections, not dimensionally stable. The connection element 45 is arranged on the pouch 56 such that the parting joint between connection element 45 and pouch 56 can ensure a preferably hermetic seal of the interior space of the pouch 56 with respect to the surroundings of the pouch bioreactor 55. Furthermore, the connection element 45 has a connection opening 30 which, in the present exemplary embodiment, has a circular cross section. The connection opening 30 is designed to receive a single-use connection device 10, 20 according to the invention. The connection opening 30 preferably has, on its inner circumferential surface, an internal thread which enables an external thread of complementary form on a single-use connection device 10, 20 to be received.

Figure 8:
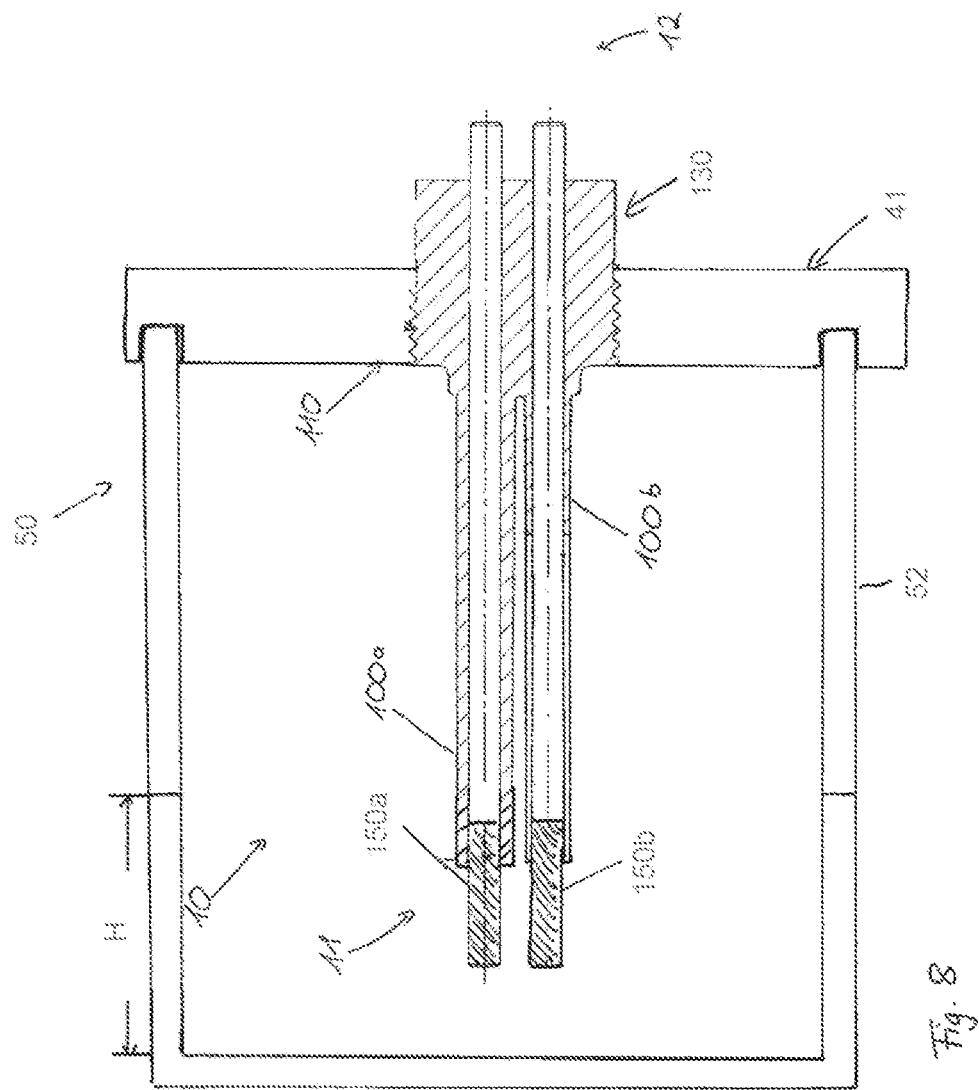
FIG. 8 shows a longitudinally sectioned sectional illustration of a further exemplary embodiment of a single-use connection device arranged in a top plate of a bioreactor.

FIG. 8 shows a longitudinally sectioned sectional illustration of a further exemplary embodiment of a single-use connection device 10, which is arranged in a top plate 41 of a bioreactor 50. The bioreactor 50 furthermore comprises a bioreactor vessel 52 to which the top plate is fastened. The single-use connection device 10 extends from an outer end 12 to an inner end 11, which projects into the bioreactor vessel 52 and thus into the bioreactor 50. The outer end 12 of the single-use connection device 10 is formed by a force admission section 130, which is designed to externally applied forces. Such forces may result in particular from the process of the single-use connection device 10 being introduced (for example by being screwed in) into the top plate 41, for example from a torque that can be applied via force admission section 130.

In a longitudinal direction in the direction of the inner end 11, a fastening section 110 with an external thread is arranged on the force admission section 130. On that end side of the fastening section 110 which faces toward the inner end 11, there are arranged two inner pipe segment 100a, 100b composed of plastic. The central axes of said two inner pipe segments 100a, 100b are arranged parallel to the central axis of the force admission section 130 and of the fastening section 110. On the ends of the inner pipe segments 100aa, 100b, there is arranged in each case one filter element 150a, 150b. The exemplary embodiment shown involves ceramic filter elements. In the embodiment shown, these ceramic filter elements 150a, 150b project beyond the inner end of the respective pipe segment. The inner pipe segments 100a, 100b may be utilized both for a supply of media or gases and for an extraction of media or a discharge of media. The ceramic filter elements ensure that no cells from the culture broth exit the bioreactor in the case of the respective pipe segment being used for a discharge of media, because said cells are retained by the filter. On the other hand, a fine-bubble distribution of the supplied gas or of the supplied medium can also be achieved by means of the ceramic filter.

Here, the pipe segments 100a, 100b are formed so as to be long enough that their respective inner end is situated below a minimum fill level H for culture medium of the bioreactor. The pipe segments 100a, 100b preferably comprise the ceramic filter elements 150a, 150b. It may therefore also suffice for only the filter elements 150a, 150b or their ends—their lower ends in the operating state—to be situated below the minimum fill level H.

It is thus ensured that the supply of media can take place directly into the culture medium. A use for discharging media is also realized advantageously if the pipe segment projects into the culture medium. To ensure this regardless of the fill level during intended use, the inner end of the pipe segments 100a, 100b is situated below the minimum fill level H. A supply or discharge of media directly into or directly out of the culture medium is thus ensured even in the presence of minimum filling.

It will be understood by one having ordinary skill in the art that construction of the described present disclosure and other components is not limited to any specific material. Other exemplary embodiments of the disclosure disclosed herein may be formed from a wide variety of materials, unless described otherwise herein.

For purposes of this disclosure, the term "operably coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

For purposes of this disclosure, the term "operably connected" (in all of its forms, connect, connecting, connected, etc.) generally means that one component functions with respect to another component, even if there are other components located between the first and second component, and the term "operable" defines a functional relationship between components.

It is also important to note that the construction and arrangement of the elements of the present disclosure as shown in the exemplary embodiments is illustrative only. Although only a few embodiments of the present innovations have been described in detail in this disclosure, those skilled in the art who review this disclosure will readily appreciate that many modifications are possible, e.g., variations in sizes, dimensions, structures, shapes and proportions of the various elements, values of parameters, mounting arrangements, use of materials, colors, orientations, etc. without materially departing from the novel teachings and advantages of the subject matter recited. For example, elements shown as integrally formed may be constructed of multiple parts or elements shown in multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of the wide variety of materials that provide sufficient strength or durability, in any of the wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is to be understood that variations and modifications can be made on the aforementioned structure and method without departing from the concepts of the present disclosure, and further it is to be understood that such concepts are intended to be covered by the following claims unless these claims by their language expressly state otherwise.

The invention claimed is:

1. A single-use connection device for a bioreactor having a reaction chamber, the single-use connection device comprising:
    a plurality of passages through the single-use connection device, the plurality of passages adapted to provide access to the reaction chamber of the bioreactor; and
    a sleeve defining an outmost circumferential surface of the single-use connection device, the sleeve comprising a fastening section comprising an outer circumferential surface having a fastening structure operably coupling the single-use connection device within a connection opening of the bioreactor when the single-use connection device is inserted into the connection opening;
    wherein the single-use connection device is formed in one piece and from plastic; and
    wherein the single-use connection device further comprises a plurality of sensors, wherein one of the plurality of sensors is formed as a fill level sensor and wherein at least two of the plurality of passages each have one of the plurality of sensors disposed therein.

2. The single-use connection device of claim 1, wherein the connection opening of the bioreactor comprises a connection opening of a top plate of a dimensionally stable bioreactor or a connection opening of a pouch bioreactor.

3. The single-use connection device of claim 1, wherein the fastening structure further comprises an external thread, ribs, projections, snap-action elements, detent elements, or depressions.

4. The single-use connection device of claim 1, wherein the sleeve further comprises an encircling stop surface that extends outward in a radial direction from the outer circumferential surface of the fastening section.

5. The single-use connection device of claim 4, wherein the sleeve further comprises a force admission section formed as a polygonal profile and which directly adjoins the stop surface.

6. The single-use connection device of claim 1, wherein at least one passage of the plurality of passages is formed at least in one section as at least one pipe segment, wherein the at least one pipe segment extends parallel to a central axis of an outer circumferential surface of the fastening section, and wherein the at least one pipe segment has one or more predetermined breaking points.

7. The single-use connection device of claim 6, wherein the at least one pipe segment is deformable under the action of heat, such that the at least one passage is closable in fluid-tight fashion as a result of a change in shape.

8. The single-use connection device of claim 6, wherein the at least one pipe segment is adapted to be closed off in at least one end by a hose-securing device.

9. The single-use connection device of claim 6, wherein the at least one pipe segment is formed from plastic and has a filter element at an end provided for insertion into the bioreactor.

10. The single-use connection device of claim 9, wherein the filter element has a pore size in a range from 0.1 μm-500 μm and is comprised of glass, porous ceramic, plastic or a filter cassette.

11. The single-use connection device of claim 10, wherein the filter element has a pore size in a range from 0.5-5 μm.

12. The single-use connection device of claim 10, wherein the filter element has a pore size in a range 5-500 μm.

13. The single-use connection device of claim 9, wherein the plastic of the at least one pipe segment is a thermoplastic, and the filter element includes aluminum oxide, zirconium oxide, borosilicate, polycarbonate, polypropylene, or polyethylene.

14. The single-use connection device of claim 1, further comprising at least one sensor or electrode, wherein the at least one sensor or electrode is arranged in one passage of the plurality of passages.

15. A single-use connection device for a bioreactor having a reaction chamber, the single-use connection device comprising:
a plurality of vertical passages through the single-use connection device, the plurality of vertical passages adapted to provide access to the reaction chamber of the bioreactor; and
a sleeve defining an outmost circumferential surface of the single-use connection device, the sleeve comprising a fastening section comprising an outer circumferential surface having a fastening structure operably coupling the single-use connection device within a connection opening of the bioreactor when the single-use connection device is inserted into the connection opening;
wherein the single-use connection device is formed in one piece and from plastic; and
wherein the single-use connection device further comprises a plurality of sensors, wherein one of the plurality of sensors is formed as a fill level sensor and wherein at least two of the plurality of vertical passages each have one of the plurality of sensors disposed therein.

\* \* \* \* \*